US007858927B2

(12) United States Patent
Thomson

(10) Patent No.: US 7,858,927 B2

(45) Date of Patent: Dec. 28, 2010

(54) APPARATUS AND METHOD FOR OPERATING A DIFFERENTIAL MOBILITY ANALYZER WITH A MASS SPECTROMETER

(75) Inventor: Bruce Thomson, Toronto (CA)

(73) Assignee: DH Technologies Development Pte, Ltd., Singapore (SG)

(*) Notice: Subject to any disclaimer, the term of this patent is extended or adjusted under 35 U.S.C. 154(b) by 210 days.

(21) Appl. No.: 12/275,597

(22) Filed: Nov. 21, 2008

(65) Prior Publication Data

US 2009/0134322 A1 May 28, 2009

Related U.S. Application Data

(60) Provisional application No. 60/989,873, filed on Nov. 23, 2007.

(51) Int. Cl.
*H01J 49/26* (2006.01)
*B01D 59/44* (2006.01)

(52) U.S. Cl. ....................... 250/281; 250/282; 250/288; 250/423 R; 250/424

(58) Field of Classification Search ................. 250/281, 250/282, 288, 423 R, 424
See application file for complete search history.

(56) References Cited

U.S. PATENT DOCUMENTS 5,869,831 A 2/1999 De La Mora et al.
5,936,242 A * 8/1999 De La Mora et al. ........ 250/288
6,700,120 B2 3/2004 Hager
6,787,763 B2 * 9/2004 De La Mora et al. ........ 250/287
2009/0101812 A1 * 4/2009 Thomson .................... 250/282

OTHER PUBLICATIONS

S. Ude et al., "Charge-Induced Unfolding of Multiply Charged Polyethylene Glycol Ions", J. Am. Chem. Soc. 2004, 126, pp. 12184-12190.

Juan Fernandez De La Mora et al., "The potential of differential mobility analysis coupled to MS for the study of very large singly and multiply charged proteins and protein complexes in the gas phase", Biotechnol. J. 2006, 1, pp. 1-10, Wiley-VCH Verlag GmbH & Co.

Juan Fernandez De La Mora et al., "Tandem Mobility Mass Spectrometry Study of Electrosprayed Tetraheptyl Ammonium Bromide Clusters", J. Am. Soc. Mass Spectrom. 2005, 16, pp. 717-732, Elsevier Inc.

* cited by examiner

*Primary Examiner*—Nikita Wells
(74) *Attorney, Agent, or Firm*—Bereskin & Parr LLP/S.E.N.C.R.L., s.r.l.

(57) ABSTRACT

An apparatus and method of analyzing ions is described in which a Differential Mobility Analyzer (DMA) is combined with an analysis device. The DMS can be operated in first and second modes of operation to produce a plurality of ions that are sampled and analyzed by the analysis device. In the first mode of operation the DMA is configured to enable ion mobility separation and the analysis device samples and analyzes ions having ion mobility in a certain range of ion mobility and in the second mode of operation the DMA is configured to disable ion mobility separation and the analysis device samples and analyzes ions without discrimination based on ion mobility.

24 Claims, 2 Drawing Sheets

APPARATUS AND METHOD FOR OPERATING A DIFFERENTIAL MOBILITY ANALYZER WITH A MASS SPECTROMETER

CROSS REFERENCES TO RELATED APPLICATIONS

This application claims the benefit of U.S. Provisional Application No. 60/989,873 filed Nov. 23, 2007, and the entire contents of which are hereby incorporated by reference.

FIELD

The various embodiments described herein generally relate to an apparatus that includes a mobility analysis device and an ion analysis device and is configured to operate in several modes of operation.

INTRODUCTION

An ion mobility analyzer is designed to separate ions based on ion mobility, and can separate ions that have different shapes or collision cross-sections. Accordingly, ion mobility can also be used to measure the collision cross-section of an ion in order to provide information about the shape of an ion. Since a Mass Spectrometer (MS) is designed to filter ions based on mass-to-charge ratio, the analysis results of a complex mixture can be enhanced when an ion mobility analyzer is combined with a MS. This is because the MS can separate species that have the same mass-to-charge ratio but different shape as well as species that have the same mass-to-charge ratio but different charge. Both of these operations can reduce chemical noise interference and increase signal-to-noise ratio.

Ion mobility analyzers generally use an electric field to drift ions through a gas in a drift region. The speed of the ions is related to the electric field by:

$$v=K\cdot E \quad (1)$$

where v is ion velocity in units of m/s, E is electric field strength in the drift region in units of V/m and K is ion mobility in units of $m^2/(V\cdot s)$. One method of separating ions by mobility is to provide a pulse of ions into the drift region and measure the flight time over a fixed distance. This requires creating a pulse of ions, which requires either wasting ions from a continuous beam or trapping them in front of pulsing regions.

Another method of separating ions by mobility is employed by a Differential Mobility Analyzer (DMA), which separates ions in space rather than in time. Ions are continuously introduced through an entrance aperture in a DMA entrance plate and then drift across a DMA drift region, which is a fixed space, to an exit aperture in a DMA exit plate. An electric field is applied between the DMA entrance plate and the DMA exit plate, i.e. across the DMA drift region. A sheath gas flow is also introduced into the DMA drift region. The DMA drift region is generally maintained at atmospheric pressure. The direction of the sheath gas flow is transverse with respect to the flow of ions such that the ions in the DMA drift region flow in a direction that is approximately perpendicular to the electric field. The faster ions reach the DMA exit plate upstream of the slower ions. A narrow DMA electrode near the DMA exit plate measures the ion current. By varying the electric field strength across the DMA drift region, ions of different mobility are swept across the DMA electrode to register an ion mobility spectrum.

The best separation efficiency (i.e. mass resolution) results when the electric field strength within the DMA drift region is very high and the width of the DMA drift region is small, so that the diffusion of the ions is minimized. This in turn requires a very high gas flow velocity under laminar flow conditions for the sheath gas flow. Flow characteristics can be characterized by the Reynolds number (Re), which is widely used in fluid mechanics.

$$Re=(\rho\cdot v\cdot D)/\mu \quad (2)$$

In equation 2, the variable $\rho$ is the gas density in $g/cm^3$, v is the gas velocity in cm/s, D is the characteristic dimension of the chamber in cm and $\mu$ is the viscosity of the gas in g/cm-sec. Gas flow becomes turbulent above a Reynolds number of 2,000. In a properly designed DMA, the laminar flow can be maintained for some distance at a Reynolds number approaching 100,000 if no flow disturbances are introduced and the walls defining the DMA drift region are smooth. Accordingly, any outflow of sheath gas can disturb the laminar sheath gas flow and the steady state pressure condition within the DMA drift region. This can affect the ion motion in the region of the outflow, causing a loss of mobility resolution for the DMA. Outflow of the sheath gas can occur at both the exit and entrance apertures of the DMA.

In current implementations that combine a DMA with a MS, ions are directly sampled from the exit aperture of the DMA into the vacuum region of the MS; i.e. the DMA exit plate is directly attached to, or serves as, the inlet plate of the MS. At a fixed electric field strength within the DMA drift region, only the ions of a particular mobility will be transmitted to the MS. If the electric field strength is scanned, a mobility spectrum can be produced. The MS can either be scanned quickly while the DMA is scanned slowly, or the MS can by set to transmit one or several ions sequentially while the DMA is scanned. Accordingly, in conventional implementations, when a DMA is coupled to a MS, ions are always separated with respect to mobility before entering the MS. In these implementations, there is no way to sample all of the ions without mobility discrimination, except by scanning the DMA voltage and acquiring mass spectra. Unfortunately, this method wastes ions.

SUMMARY

In a first aspect, at least one embodiment described herein provides a method of providing a Differential Mobility Analyzer (DMA) that can operate in several modes of operation. The method comprises providing a chamber having a first plate with first and second inlet apertures and a second plate with an exit aperture, the second plate being located relative to the first plate to define a DMA drift region. The method further comprises providing the first inlet aperture at a position that is generally opposite to and aligned with the exit aperture and a second inlet aperture at a position that is offset with respect to the exit aperture, providing a laminar gas flow element that is operable to create a sheath gas flow in the DMA drift region when provided with a gas flow during use; and configuring the DMA to receive voltages, wherein during use, the voltages are applied to the DMA to generate an electric field between the first and second plates. During use, in a first mode of operation sample ions provided to the second inlet aperture are separated based on mobility to provide a portion of the sample ions to the exit aperture, and in a second mode of operation another portion of sample ions provided to the first inlet aperture are provided to the exit aperture without mobility separation.

In a further aspect, at least one embodiment described herein provides a DMA comprising a chamber comprising a first plate with first and second inlet apertures and a second plate with an exit aperture, the second plate being located relative to the first plate to define a DMA drift region, the first inlet aperture being at a position that is generally opposite to and aligned with the exit aperture and the second inlet aperture being at a level that is offset with respect to the exit aperture. The DMA further comprises a laminar gas flow element that is operable to create a sheath gas flow in the DMA drift region when provided with a gas flow during use; and first and second voltage contacts configured to receive voltages to generate an electric field between the first and second plates during use. The DMA is configurable to operate in a first mode of operation in which sample ions provided to the second inlet aperture are separated based on mobility to provide a portion of the sample ions to the exit aperture, and in a second mode of operation another portion of sample ions provided to the first inlet aperture are provided to the exit aperture without undergoing separation based on mobility.

In another aspect, at least one embodiment described herein provides a method of analyzing ions. The method comprises providing a Differential Mobility Analyzer (DMA) with a first plurality of ions; operating the DMA in first and second modes of operation to produce a second plurality of ions from the first plurality of ions; and sampling and analyzing the second plurality of ions with an analysis device. In the first mode of operation the DMA is configured to enable ion mobility separation and the analysis device samples and analyzes ions having a certain mobility and in the second mode of operation the DMA is configured to disable ion mobility separation and the analysis device samples and analyzes ions without discrimination based on ion mobility.

In yet another aspect, at least one embodiment described herein provides an apparatus for analyzing ions. The apparatus comprises a Differential Mobility Analyzer (DMA) that is configured to operate in first and second modes of operation to produce a second plurality of ions from a first plurality of ions; and an analysis device that is configured to sample and analyze the second plurality of ions. In the first mode of operation the DMA is configured to enable ion mobility separation and the analysis device is configured to sample and analyze ions having a certain mobility and in the second mode of operation the DMA is configured to disable ion mobility separation and the analysis device is configured to sample and analyze ions without discrimination based on ion mobility.

Further aspects and features of the embodiments described herein will appear from the following description taken together with the accompanying drawings.

BRIEF DESCRIPTION OF THE DRAWINGS

The skilled person in the art will understand that the drawings, described below, are for illustration purposes only and that they are not intended to limit the scope of the applicant's teachings in any way. For a better understanding of the various embodiments described herein, and to show more clearly how the various embodiments described herein may be carried into effect, reference will be made, by way of example, to the drawings in which.

DESCRIPTION OF THE VARIOUS EMBODIMENTS

Figure 1:
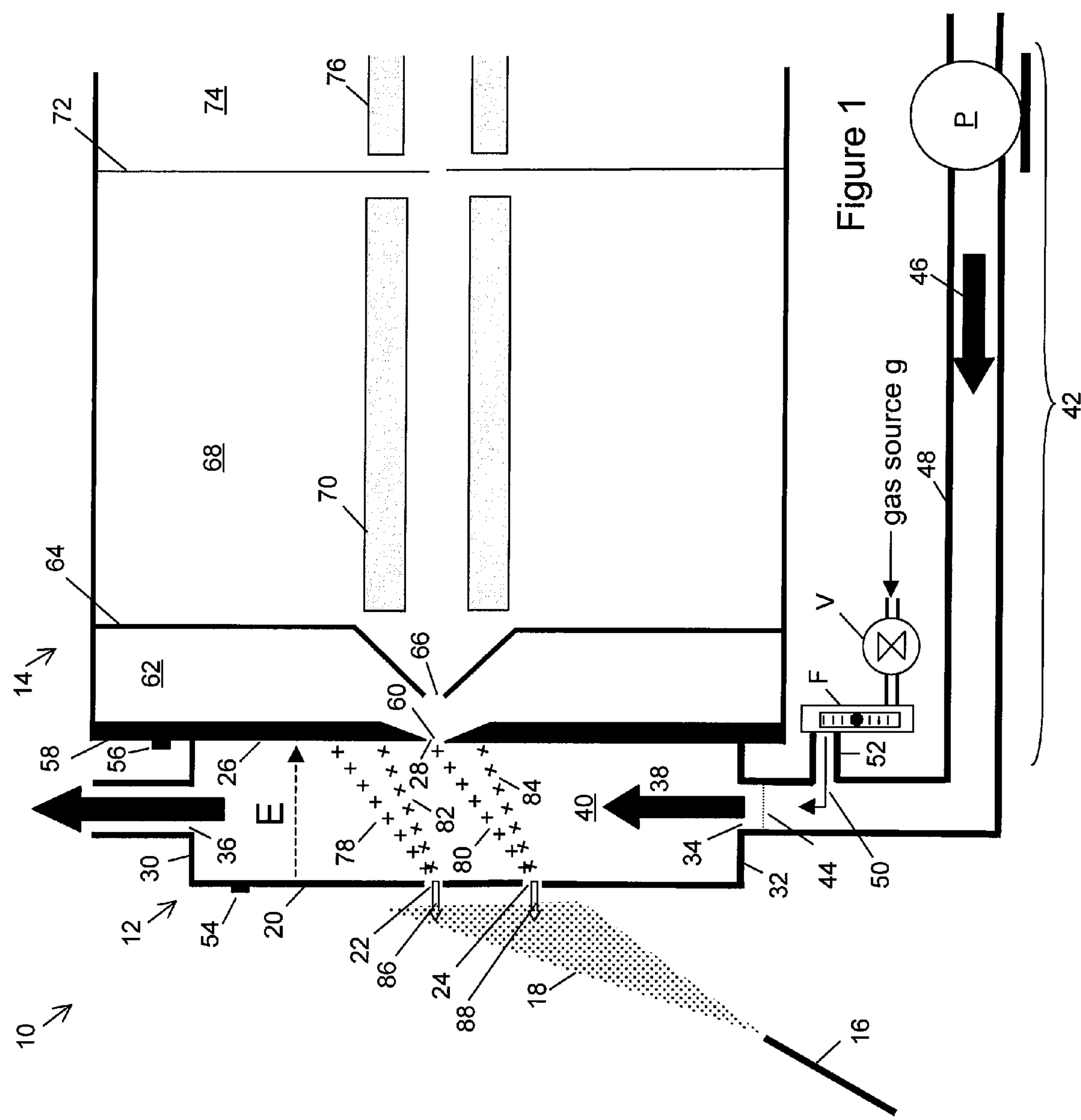
FIG. 1 is a schematic illustration of an exemplary embodiment of an apparatus that combines a DMA with a MS and is operating in a first mode of operation in which ion mobility separation is enabled.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description of the various examples provided herein is meant to further an understanding of various aspects of the applicant's teachings and should not be construed as limiting the scope of the present teachings in any way.

Referring now to FIG. 1, shown therein is a schematic illustration of an exemplary embodiment of an apparatus 10 that combines a Differential Mobility Analyzer (DMA) 12 with a Mass Spectrometer (MS) 14 and is operating in a first mode of operation in which ion mobility separation is enabled. Actually, the DMA can operate in several modes of operation, as explained below. An ion source 16 provides a plurality of sample ions 18 that are received by the DMA 12, separated in terms of ion mobility and a portion of the sample ions are then provided to the MS 14 for analysis. It should be understood that only portions of the DMA 12, MS 14 and ion source 16 are shown in FIG. 1.

The ion source 16 generates the plurality of sample ions 18 from a sample. The sample ions 18 have various charges and include certain types of ions that are to be analyzed. Examples of the ion source 16 include, but are not limited to, an electrospray ion source, an Atmospheric Pressure Chemical Ionization (APCI) ion source, an atmospheric pressure Matrix Assisted Laser Desorption Ionization ion source (MALDI), an Atmospheric Pressure PhotoIonization (APPI) ion source, a Desorption ElectroSpray Ionization (DESI) ion source, and the like.

The DMA 12 comprises a DMA entrance plate 20 with inlet apertures 22 and 24, and a DMA exit plate 26 with an exit aperture 28. The inlet and exit apertures 22, 24 and 28 can be formed as slits in the DMA entrance and exit plates 20 and 26 respectively. It should be understood that the DMA 12 generally comprises an enclosed chamber, save for the elements required for creating and re-circulating a sheath gas flow, and FIG. 1 only shows a side view of a portion of the chamber. This chamber also includes a top wall 30, a bottom wall 32 and two side walls (not shown) that connect to the DMA entrance and exit plates 20 and 26 to form a generally enclosed space for the chamber save for the entrance and exit apertures 34 and 36 for a sheath gas flow 38. The DMA entrance and exit plates 20 and 26 are located relative to one another to define a DMA drift region 40 there between. Also shown are portions of a loop near the top and bottom walls 30 and 32 for circulating the sheath gas flow through the DMA 12.

The DMA 12 also includes a gas assembly 42 and a laminar gas flow element 44 for generating the sheath gas flow 38 which is then provided to the DMA drift region 40. The gas assembly 42 is configured to provide a gas flow 46 to the laminar gas flow element 44 which then laminarizes the gas flow 46 to produce the sheath gas flow 38. The gas assembly 42 can comprise an air pump P and a piping assembly 48 as shown in FIG. 1. The air pump P can provide high flows of gas, and can be configured to disable or reduce the gas flow 46 as desired. This can be done by controlling the speed of the air pump P. Alternatively, a bypass valve (not shown) can be used to divert at least a portion of the gas flow 46 in order to reduce it as is commonly known by those skilled in the art. There is an additional piping assembly (not shown) to form a continuous flow of gas through the DMA 12 typically in the range of 10 to 100 L/s in the first mode of operation. The DMA drift region 40 is generally maintained at atmospheric pressure. The laminar gas flow element 44 helps to remove any turbulence from the sheath gas flow 38 in the DMA drift region 40. The laminar gas flow element 44 can include one or more screens (not shown in detail) to produce the sheath gas flow 38. Although the DMA 12 is shown as a rectangular chamber in FIGS. 1 and 2, it is usually necessary to provide a smooth converging region (not shown) towards the central region of the DMA 12 and a smooth diverging region (not shown) after the central region of the DMA 12. A rapid and smooth contraction of the flow area is used in order to maintain the laminar flow at a high Reynolds number. Methods for providing a laminar flow at high Reynolds number are described in U.S. Pat. No. 7,787,763. Those skilled in the art are familiar with how to implement the laminar gas flow element 44.

The sheath gas flow 38 is maintained as pure and clean as possible to minimize reactions and clustering for the sample ions that are in the DMA drift region 40. If the width of the DMA drift region 40 is 0.5 cm, achieving a Re number greater than 20,000 can require a gas flow of up to 2,800 L/min. Since pure gas cannot easily be supplied at that rate, the sheath gas flow 38 is re-circulated after purifying the environment by introducing an auxiliary flow of clean gas 50 into the closed loop by using an auxiliary gas assembly comprising a gas source g, a valve V, an adjustable flowmeter F and a piping assembly 52. The auxiliary gas assembly is optional and not needed for the operation of the DMA 12, but it helps improve the DMA resolution when the DMA 12 is operating in ion mobility mode, because it increases the purity of the sheath gas flow 38 (as described above) and thereby reduces the formation of adducts and clusters in the DMA 14. Adducts and clusters contribute to the formation of additional peaks in the DMA spectrum, and can broaden the mobility peak of the ion of interest. The auxiliary flow of gas 50 is not sufficient to provide ion mobility separation. In addition, any leak outward of the sheath gas flow 38, into the ion source region for example, can be compensated by the addition of this auxiliary flow of clean gas 50 in order to maintain the steady-state pressure throughout the loop. Suction of gas into the MS 14 constitutes a leak and can be made up by also adding gas to the sheath gas flow 38. Alternatively, or in addition, an interface region can be used which is described in Applicant's provisional patent application No. 60/980,837 filed on Oct. 18, 2007.

In at least some implementations, a sufficient amount of the auxiliary gas flow 50 is added to the sheath gas flow 38 such that there is a gas outflow 86 and 88 from the DMA drift region 40 into the ion source region. This prevents the gas and particles from the ion source 16 from entering the DMA drift region 40 where ion separation takes place, and helps to maintain the purity of the sheath gas flow 38. By adjusting the amount of the auxiliary gas flow 50 that is added to the sheath gas flow 38, the pressure in front of the apertures 22 and 24 can be controlled so that there is a slight outflow into the ion source region. This provides a gas curtain barrier that keeps any gas from the ion source 16 out of the DMA drift region 40. The valve V and the adjustable flowmeter F can be used to control the auxiliary gas flow 50.

The DMA entrance and exit plates 20 and 26 also include voltage contacts 54 and 56 respectively that are configured to receive voltages V1 and V2 during use. The electric field E across the DMA drift region 40 between the DMA entrance and exit plates 20 and 26, is produced by the voltage difference between the magnitude of the voltages V1 and V2. Accordingly, the voltage contacts 54 and 56 are connected to a voltage source as is commonly known by those skilled in the art. The direction of the electric field E is generally perpendicular to the direction of the sheath gas flow 38. Conventional power supplies can be used as is commonly known by those skilled by the art to provide the voltages V1 and V2 and hence are not shown.

The inlet aperture 22 is located generally opposite to and aligned with the exit aperture 28. The inlet aperture 22 is located downstream of the inlet aperture 24 so that it does not disturb the sheath gas flow 38 when the DMA 12 is in operation. The geometry of the inlet aperture 22 is typically a slit of the same geometry as the inlet aperture 24, but it can also be a circular aperture in alternative embodiments. The inlet apertures 22 and 24 are offset in the direction of the sheath gas flow 38 and the amount of offset depends on the particular design used for the DMA 12 as well as the amount of the sheath gas flow 38, the strength of the electric field E and the length of the DMA drift region 40 (i.e. the distance between the DMA entrance and exit plates 20 and 26). The inlet aperture 24 is also at a position that is offset with respect to the exit aperture 28. If the exit aperture 28 is formed as a slit, the major axis of the slit (i.e. its length) is typically oriented perpendicular to the direction of the sheath gas flow 38.

The MS 14 includes an orifice plate 58 with an inlet aperture 60, a first vacuum region 62, a skimmer plate 64 with a conical orifice 66, a second vacuum chamber 68 and a first multipole rod set 70. The MS 14 also includes a plate 72, a third vacuum chamber 74 and a second multipole rod set 76. The first vacuum region 62 can be a differentially pumped vacuum chamber that has a pressure of approximately 0.133 kPa and the second vacuum chamber 68 can be evacuated to a lower pressure at approximately 0.00133 kPa. The third vacuum chamber 74 is typically at an even lower pressure at approximately $1.3\times10^{-6}$ kPa. The first multipole rod set 70 is typically an RF ion guide and the second multipole rod set 76 can receive DC and RF voltages and provide mass resolving functionality. Conventional power supplies, and pumps, including roughing pumps and turbo pumps, can be used as is commonly known by those skilled by the art and hence are not shown. Other configurations and pressures can be used for the MS 14 as is commonly known by those skilled in the art. For example, the MS 14 can be, but is not limited to, a quadrupole MS, a triple quadrupole MS, an ion trap MS, a Quadrupole-quadrupole Time Of Flight (QqTOF) MS, a Fourier Transform MS, a magnetic sector MS and the like.

The DMA 12 and the MS 14 can be produced as a single unit. In this case, the DMA exit plate 26 and the orifice plate 58 are provided by the same structure and the exit aperture 28 and the inlet aperture 60 are the same aperture. This embodiment is shown in FIG. 1. In alternative embodiments, the DMA 12 and the MS 14 are produced as separate units and are then connected so that the exit aperture 28 is aligned with the inlet aperture 60.

In use, the sample ions 18 are generated by the ion source 16 and directed towards the inlet apertures 22 and 24 in the DMA entrance plate 20. Once the sample ions 18 are inside the DMA drift region 40, they are subjected to the sheath gas flow 38 and the electric field E. As the sample ions move across the DMA drift region 40, the sheath gas flow 38 carries the sample ions in a direction generally perpendicular to the electric field E. The combined gas and electric-field-driven motion cause the sample ions to move at an angle. This separates the sample ions 18 into mobility separated ions including higher mobility sample ions 78 and 80 and lower mobility sample ions 82 and 84 as is known by those skilled in the art. If the angle is correct, a portion of the sample ions, in this case sample ions 80, will reach the exit aperture 28 and be sampled into the MS 14.

The angle taken by a sample ion within the DMA 12 is defined by the ratio $v_d/v_g$ where $v_d$ is the drift velocity of the sample ion due to the strength of the electric field E and $v_g$ is the sheath gas velocity. Since $v_d = k \cdot E$ where k is the ion mobility, then the angle of motion θ depends on the sample ion mobility as shown in equation 3.

$$\tan(\theta) = v_g/(k \cdot E) \tag{3}$$

By adjusting the voltage V2 while leaving the voltage V1 fixed, sample ions of a specific mobility can be transmitted into the MS 14 while sample ions of other mobilities are rejected. A DMA spectrum can be produced by scanning or ramping the voltage V2.

In the example shown in FIG. 1, the voltages V1 and V2 have been selected such that higher mobility sample ions 78 and the lower mobility sample ions 82 and 84 are directed by the sheath gas flow 38 such that they cannot exit through the exit aperture 28. However, the higher mobility sample ions 80 are displaced upwards by the correct amount by the sheath gas flow 38 so that these ions can exit through the exit aperture 28.

Figure 2:
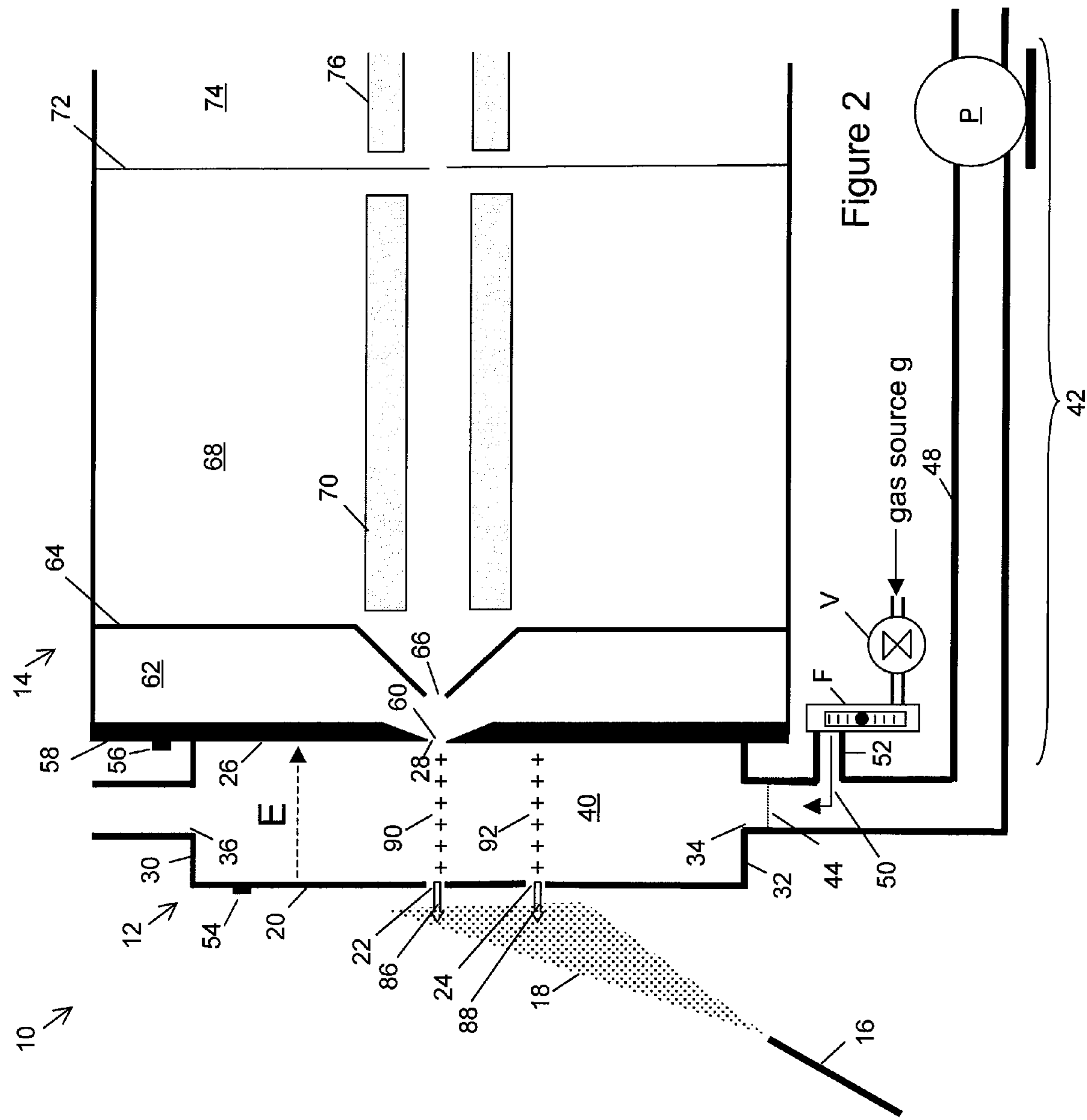
FIG. 2 is a schematic illustration of the apparatus of FIG. 1 operating in a second mode of operation in which ion mobility separation is disabled.

Referring now to FIG. 2, shown therein is a schematic illustration of the apparatus 10 operating in a second mode of operation in which ion mobility separation is disabled. In this case, the gas assembly 42 has been configured to turn off or sufficiently reduce the gas flow 46 to disable the ion mobility separation functionality of the DMA 12. The gas assembly 42 can be under software control to automatically electronically disable and re-enable the DMA ion mobility separation function. This allows an operator to readily turn the DMA function on or off without having to make any hardware changes.

In this case, the sample ions are separated into a first portion of sample ions 90 and a second portion of sample ions 92. Since the inlet aperture 24 is offset from the exit aperture 28, the portion of sample ions 92, which are also not separated in terms of ion mobility, hit the DMA exit plate 26. However, since the inlet aperture 22 is generally opposite the exit aperture 28, the portion of sample ions 90, having different types of ion mobility, are sampled without discrimination, i.e. without mobility separation, into the MS 14.

Accordingly, in this exemplary embodiment, the DMA 12 can be either turned on, in order to separate different sample ion species by their mobility and detect sample ions of only a certain mobility, or turned off so that sample ions of all different types of ion mobilities can be analyzed without discrimination into the MS 14. This allows survey scans of all sample ions from the ion source 16 to be sampled, just as in an analysis system without a DMA interface. This can be used in analytical situations in which the target ions are unknown, and a full scan mass spectrum can be obtained without the need to sweep the DMA voltage. It should be understood that the term "certain mobility" means ions having a mobility that is in a range of ion mobilities that corresponds to ions that are desired to be analyzed.

Accordingly, the apparatus 10 allows an operator to see the entire mass spectrum for a sample without using mobility separation. This may also be done using a conventional DMA, but the end result in some duty cycle loss, because the DMA voltage has to be ramped over a wide range to sequentially transmit ions of different mobility. Alternatively, with the apparatus 10, to obtain a survey scan, in which sample ions of all mobilities from the source are analyzed, the DMA ion mobility separation function can be easily turned off or disabled. Then to analyze specific ion masses, the DMA ion mobility separation function can be easily enabled and configured for these specific ion masses. The speed with which the DMA ion mobility separation function can be turned on and off depends on how fast the gas flow 46 can be turned on and off.

Different strengths for the electric field E can be used in the first and second modes of operation. For example, in the second mode of operation, the strength of the electric field E can be adjusted to achieve improved sensitivity for the analysis performed by the MS 14. Generally, the lower the strength of the electric field E, the longer the time that it takes for the sample ions 90 to cross the DMA drift region 40, and the more diffusion and ion losses that will be experienced. Using the additional inlet aperture 22 opposite the exit aperture 28 allows for the use of a higher strength for the electric field E to minimize sample ion losses, without getting any ion mobility separation. Typical values for the magnitude of the electric field E range from 1,000 V/cm up to 8,000 V/cm in the second mode of operation.

Accordingly, in the second mode of operation, a first set of voltages can be applied to the DMA entrance and exit plates 20 and 26 to guide ions from the DMA entrance aperture 22 to the DMA exit aperture 28. In the first mode of operation, a second set of voltages can be applied to the DMA plates 20 and 26 to generate the electric field E between the first and second plates 20 and 26 to guide mobility separated ions from the second entrance aperture 24 to the exit aperture 28 in a direction generally perpendicular with respect to the sheath gas flow 38. The first and second set of voltages can be selected to create electric fields having similar or different magnitudes.

In alternative embodiments, the DMA 12 can be used with downstream analysis devices other than a mass spectrometer. For example, the DMA 12 can be used with another DMA or mobility device.

In other alternative embodiments, the position of the ion source 16 can be adjusted for the different modes of operation of the DMA 12 to line it up better with one of the inlet apertures in the DMA entrance plate 20 from which the sample ions are ultimately provided to the DMA exit plate 26. For example, when the DMA ion mobility separation function is turned on, the ion source 16 can be positioned such that more of the sample ions 18 enter through the inlet aperture 24 than through the inlet aperture 22. Conversely, when the DMA ion mobility separation function is turned off, the ion source 16 can be repositioned so that more of the sample ions 18 enter through the inlet aperture 22 than through the inlet aperture 24.

In the second mode of operation, the auxiliary gas flow 50 can be maintained in order to provide a curtain gas barrier. In this mode, the gas flow 46 is turned off, and ions 90 are sampled from the ion source 16 through apertures 22 and 28 and then into the MS 16. An electric field can be provided to transport the ions through the DMA drift region 40, but without the sheath gas flow 38, there is no mobility separation. The aperture 22 can be a slit of the same dimensions as aperture 28 (typically 0.2 to 0.5 mm in width, and between 10 and 30 mm long), or the aperture 22 can be a wider slit than the aperture 28, for example the aperture 22 can be 1 to 3 mm wide, in order to improve the sensitivity. Alternatively, the aperture 22 can be a round orifice with a diameter of approximately 3 mm similar to orifices that are typically used in the curtain gas plate of a conventional MS system. The shape of the aperture 22 is not a critical parameter as long as the aperture 22 is at least as large and preferably larger than the aperture 28 in order to maximize ion transmission. The auxiliary gas flow 50 in this mode of operation is typically between 1 and 10 L/m and should be larger than the flow into the vacuum region 62 through the aperture 28 (which depends on the area of aperture 22). For example, a slit that is 0.2 mm wide and 1 mm long results in gas flow of 2.3 atmospheric L/min into the vacuum region 62. In this case, the auxiliary gas flow 50 can be greater than 2.3 L/min in order to provide some outflow into the ion source region. For example, the auxiliary gas flow 50 might typically be 4 L/min in this case, but it can be adjusted using the adjustable flowmeter F to provide more sensitivity.

While the applicant's teachings are described in conjunction with various embodiments, it is not intended that the applicant's teachings be limited to such embodiments. On the contrary, the applicant's teachings encompass various alternatives, modifications and equivalents, as will be appreciated by those of skill in the art, the general scope of which is defined in the appended claims. For example, the teachings herein can be combined with the interface region described in Applicant's provisional patent application No. 60/980,837 filed on Oct. 18, 2007.

The invention claimed is:

1. A method of providing a Differential Mobility Analyzer (DMA) that can operate in several modes of operation, wherein the method comprises:

providing a chamber having a first plate with first and second inlet apertures and a second plate with an exit aperture, the second plate being located relative to the first plate to define a DMA drift region;

providing the first inlet aperture at a position that is generally opposite to and aligned with the exit aperture and a second inlet aperture at a position that is offset with respect to the exit aperture;

providing a laminar gas flow element that is operable to create a sheath gas flow in the DMA drift region when provided with a gas flow during use; and configuring the DMA to receive voltages, wherein during use, the voltages are applied to the DMA to generate an electric field between the first and second plates, wherein, during use, in a first mode of operation sample ions provided to the second inlet aperture are separated based on mobility to provide a portion of the sample ions to the exit aperture, and in a second mode of operation another portion of sample ions provided to the first inlet aperture are provided to the exit aperture without mobility separation.

2. The method of claim 1, wherein the method comprises providing a gas assembly that is configurable to provide a variable amount of the gas flow, wherein during use the gas assembly is configured to disable the gas flow in the second mode of operation.

3. The method of claim 1, wherein the method comprises providing a gas assembly that is configurable to provide a variable amount of the gas flow, wherein during use the gas assembly is configured to sufficiently reduce the gas flow to disable ion mobility separation in the second mode of operation.

4. The method of claim 2, wherein, during use, the method comprises applying a first set of voltages to the DMA to generate an electric field between the first and second plates to guide ions from the first entrance aperture to the exit aperture in the second mode of operation.

5. The method of claim 4, wherein, during use, the method comprises applying a second set of voltages to the DMA to generate an electric field between the first and second plates to guide mobility separated ions from the second entrance aperture to the exit aperture in a direction generally perpendicular with respect to the sheath gas flow in the first mode of operation, and the first and second set of voltages are selected to create electric fields having similar or different magnitudes.

6. The method of claim 1, wherein the method comprises locating the first inlet aperture downstream of the second inlet aperture with respect to sheath gas flow direction.

7. The method of claim 2, wherein the method further comprises providing an auxiliary flow of gas to the DMA during use, wherein the auxiliary flow of gas is not sufficient to provide ion mobility separation.

8. A Differential Mobility Analyzer (DMA) comprising:

a chamber comprising a first plate with first and second inlet apertures and a second plate with an exit aperture, the second plate being located relative to the first plate to define a DMA drift region, the first inlet aperture being at a position that is generally opposite to and aligned with the exit aperture and the second inlet aperture being at a level that is offset with respect to the exit aperture;

a laminar gas flow element that is operable to create a sheath gas flow in the DMA drift region when provided with a gas flow during use; and first and second voltage contacts configured to receive voltages to generate an electric field between the first and second plates during use, wherein, the DMA is configurable to operate in a first mode of operation in which sample ions provided to the second inlet aperture are separated based on mobility to provide a portion of the sample ions to the exit aperture, and in a second mode of operation another portion of sample ions provided to the first inlet aperture are provided to the exit aperture without undergoing separation based on mobility.

9. The analyzer of claim 8, wherein the analyzer further comprises a gas assembly that is configurable to provide a variable amount of the gas flow, wherein during use the gas assembly is configured to disable the gas flow in the second mode of operation.

10. The analyzer of claim 8, wherein the analyzer further comprises a gas assembly that is configurable to provide a variable amount of the gas flow, wherein during use the gas assembly is configured to sufficiently reduce the gas flow to disable ion mobility separation in the second mode of operation.

11. The analyzer of claim 8, wherein the first inlet aperture is located downstream of the second inlet aperture with respect to sheath gas flow direction.

12. The analyzer of claim 9, wherein the apparatus further comprises an auxiliary gas assembly configured to provide an auxiliary flow of gas to the DMA during use, wherein the auxiliary flow of gas is not sufficient to provide ion mobility separation.

13. A method of analyzing ions, wherein the method comprises:

providing a Differential Mobility Analyzer (DMA) with a first plurality of ions;

operating the DMA in first and second modes of operation to produce a second plurality of ions from the first plurality of ions; and sampling and analyzing the second plurality of ions with an analysis device, wherein in the first mode of operation the DMA is configured to enable ion mobility separation and the analysis device samples and analyzes ions having a certain mobility and in the second mode of operation the DMA is configured to disable ion mobility separation and the analysis device samples and analyzes ions without discrimination based on ion mobility.

14. The method of claim 13, wherein the method comprises providing the DMA with first and second inlet apertures and an exit aperture, the first inlet aperture being at a position that is generally opposite to and aligned with the exit aperture and the second inlet aperture at a level that is offset with respect to the exit aperture.

15. The method of claim 14, wherein the method comprises turning off gas flow to the DMA in the second mode of operation.

16. The method of claim 14, wherein the method comprises sufficiently reducing gas flow to the DMA to disable ion mobility separation in the second mode of operation.

17. The method of claim 14, wherein the method comprises locating the first inlet aperture downstream of the second inlet aperture with respect to sheath gas flow direction.

18. The method of claim 13, wherein the method further comprises providing an auxiliary flow of gas to the DMA during use, wherein the auxiliary flow of gas is not sufficient to provide ion mobility separation.

19. An apparatus for analyzing ions, wherein the apparatus comprises:

a Differential Mobility Analyzer (DMA) that is configured to operate in first and second modes of operation to produce a second plurality of ions from a first plurality of ions; and an analysis device that is configured to sample and analyze the second plurality of ions, wherein in the first mode of operation the DMA is configured to enable ion mobility separation and the analysis device is configured to sample and analyze ions having a certain mobility and in the second mode of operation the DMA is configured to disable ion mobility separation and the analysis device is configured to sample and analyze ions without discrimination based on ion mobility.

20. The apparatus of claim 19, wherein the DMA comprises first and second inlet apertures and an exit aperture, the first inlet aperture being at a position that is generally opposite to and aligned with the exit aperture and the second inlet aperture at a level that is offset with respect to the exit aperture.

21. The apparatus of claim 20, wherein gas flow to the DMA is turned off in the second mode of operation.

22. The apparatus of claim 20, wherein gas flow to the DMA is sufficiently reduced to disable ion mobility separation in the second mode of operation.

23. The apparatus of claim 20, wherein the first inlet aperture is located downstream of the second inlet aperture with respect to sheath gas flow direction.

24. The apparatus of claim 19, wherein the apparatus further comprises an auxiliary gas assembly configured to provide an auxiliary flow of gas to the DMA during use, wherein the auxiliary flow of gas is not sufficient to provide ion mobility separation.

* * * * *